(12) United States Patent
Korhnak et al.

(10) Patent No.: US 10,269,085 B2
(45) Date of Patent: Apr. 23, 2019

(54) MODES AND WORKFLOWS FOR PROCESSING MEDICATION REQUESTS

(75) Inventors: Daniel J. Korhnak, North Huntingdon, PA (US); Russ Gadagno, Harrison City, PA (US); Eric Kepes, Wexford, PA (US); Chayla Whaley, Valencia, PA (US); Douglas J. Moon, Enon Valley, PA (US)

(73) Assignee: AESYNT INCORPORATED, Cranberry Township, PA (US)

( * ) Notice: Subject to any disclaimer, the term of this patent is extended or adjusted under 35 U.S.C. 154(b) by 750 days.

(21) Appl. No.: 12/980,751

(22) Filed: Dec. 29, 2010

(65) Prior Publication Data

US 2012/0173255 A1 Jul. 5, 2012

(51) Int. Cl.
| | |
|---|---|
| G06F 19/00 | (2018.01) |
| G06Q 10/06 | (2012.01) |
| G06Q 10/10 | (2012.01) |
| G06Q 50/22 | (2018.01) |

(52) U.S. Cl.
CPC ............. *G06Q 50/22* (2013.01); *G06F 19/00* (2013.01); *G06Q 10/06* (2013.01); *G06Q 10/103* (2013.01); *Y04S 10/54* (2013.01)

(58) Field of Classification Search
None
See application file for complete search history.

(56) References Cited

U.S. PATENT DOCUMENTS

| | | | | |
|---|---|---|---|---|
| 4,847,764 A | * | 7/1989 | Halvorson | ............ G06F 19/326 700/231 |
| 5,933,810 A | | 8/1999 | Okawa | |
| 6,181,979 B1 | * | 1/2001 | Murakami | ............ G06Q 10/06 700/216 |
| 6,832,202 B1 | | 12/2004 | Schuyler et al. | |
| 7,003,475 B1 | * | 2/2006 | Friedland | ............... G06Q 10/06 705/7.13 |
| 7,084,737 B1 | | 8/2006 | Moore et al. | |
| 7,707,075 B2 | | 4/2010 | Vaughan et al. | |
| 7,860,724 B2 | * | 12/2010 | Chudy et al. | ..................... 705/2 |
| 7,865,420 B1 | | 1/2011 | Daman et al. | |
| 8,032,397 B2 | * | 10/2011 | Lawless | .............. G06F 19/3418 705/3 |
| 2004/0088187 A1 | * | 5/2004 | Chudy | ................... G06Q 10/10 705/2 |

(Continued)

OTHER PUBLICATIONS

McKesson, "Guide to Reports—Connect Rx Version 6.8" Dec. 2008.*

(Continued)

*Primary Examiner* — Neal Sereboff
(74) *Attorney, Agent, or Firm* — Alston & Bird LLP

(57) ABSTRACT

Systems, methods, apparatus, and computer program products are provided for processing medication requests. In one embodiment, a user may define an operational mode that can be initiated by one or more triggers. A user may also define one or more workflows for processing medication requests. The one or more workflows can be associated with the operational mode. In response to the occurrence of the appropriate triggers, the operational mode can automatically, semi-automatically, and/or manually be initiated. When the operational mode is initiated, the associated workflows are used for processing medication requests.

18 Claims, 7 Drawing Sheets

(56) References Cited

U.S. PATENT DOCUMENTS

| | | | | |
|---|---|---|---|---|
| 2005/0187948 | A1* | 8/2005 | Monitzer | G06F 19/00 |
| 2006/0265286 | A1 | 11/2006 | Evangelist et al. | |
| 2007/0250346 | A1* | 10/2007 | Luciano, Jr. | A61J 7/0069 705/2 |
| 2007/0267430 | A1* | 11/2007 | Luciano, Jr. | A61J 7/0069 221/2 |
| 2008/0306740 | A1* | 12/2008 | Schuck | G06Q 50/22 704/275 |
| 2010/0257105 | A1 | 10/2010 | Wurster | |
| 2011/0258014 | A1* | 10/2011 | Evangelist | G06Q 10/06313 705/7.23 |

OTHER PUBLICATIONS

McKesson, "Case Study—Evergreen Hospital Medical Center" Aug. 2007.*
McKesson, "Data Solution Overview Brochure" Mar. 2009.*
McKesson, CarePoint Connect Sep. 2009.*
McKesson, "AcuDose-Rx Info" 2004.*
McKesson, "Anesthesia-Rx" Feb. 2009.*
PP&P, "Automated Dispensing Cabinets Buyers Guide" Sep. 2006.*
Shack & Tulloch, "Case Study—Shore Memorial Hospital" 2008.*
Shack&Tulloch, "Case Study—St. Dominic-Jackson Memorial Hospital" 2007.*
Falkenholm, "Carousels—The Next Step in Closed Loop Inventory Control" Sep. 11, 2009.*
Shack&Tulloch, "Case Study—Appalachian Regional Healthcare" 2008.*
Simpon, "Open Matrix and Detecting Drawers for McKesson's AcuDose-Rx Cabinets" Jun. 2008, PP&P.*
New Hanover Regional Medical Center, "AdminRx" Summer 2007.*
McKesson, "IntelliShelf-Rx" Sep. 2009.*
McKesson, "intelliShelf-Rx Make your shelves smart and your inventory electronic" Mar. 2007.*
McKesson, "Packaging Solutions" Mar. 2009.*
McKesson, "Horizon MedComm-Rx" Mar. 2009.*
McKesson, "Fulfill-Rx" May 2009.*
McKesson, "Robot-Rx" Aug. 2009.*
Remstar, "Pharmacies using Remstar Solutions—McKesson pharmacy automation" May 2009.*
McKesson, "Pharmacy Automation" Jul. 13, 2009.*
Weizer, Pharmacy Purchasing and Products, "The Bigger packaging pricture, PACMED".*
Wood, "Case Study—Improving medication management and lowering drug costs through automated drug dispensing" pharmacy purchasing and products, Apr. 2007.*
Reed, Neil, "Benefits of Automation in Medication Delivery: A community Hospital's Experience" 105th-112th Congress (1997-Present)—Hearings—Special Committee on Aging, May 3, 2001.
McKesson, "PROmanager-Rx" Oct. 2009.
Wurman, et al., "Coordinating Hundreds of Cooperative, Autonomous Vehicles in Warehouses" Association for the Advancement of Artificial Intelligence 2007.
McKesson, "Performance Strategies" vol. 2 Issue 3, 2008.
McKesson, "Case Study—Phoebe Putney Memorial Hospital" 2005.
Yu, "Enhancing Warehouse Performance by Efficient Order Picking" Erasmus Research Institute of Management PhD 2008.
Aberdeen Group, "Supply Chain Inventory Strategies Benchmark Report" Dec. 2004.
McKesson, "Horizon Admin-Rx" Aug. 2005.
McKesson, "Horizon Meds Manager" Jul. 2007.
McKesson, "Case Study—Mississippi Baptist Medical Center" 2005.
McKesson, "Case Study—Cookeville Regional Medical Center" Jun. 2008.
United States Patent and Trademark Office, Office Action for U.S. Appl. No. 12/980,728, dated Oct. 19, 2013, 23 pages, USA.
United States Patent and Trademark Office, Office Action for U.S. Appl. No. 12/980,728, dated Feb. 21, 2013, 23 pages, USA.
United States Patent and Trademark Office, Office Action for U.S. Appl. No. 12/980,747, dated Feb. 20, 2013, 17 pages, USA.
United States Patent and Trademark Office, Office Action for U.S. Appl. No. 12/980,747, dated May 30, 2013, 16 pages, USA.
Canadian Intellectual Property Office, Requisition by the Examiner for Application No. 2,759,517, Dec. 16, 2013, 2 pages, Canada.
Canadian Intellectual Property Office, Requisition by the Examiner for Application No. 2,759,513, Dec. 17, 2013, 3 pages, Canada.
Canadian Intellectual Property Office, Requisition by the Examiner for Application No. 2,759,515, Jan. 6, 2014, 2 pages, Canada.
United States Patent and Trademark Office, Office Action for U.S. Appl. No. 12/980,728, dated Apr. 24, 2014, 33 pages, USA.
Canadian Intellectual Property Office, Requisition by the Examiner for Application No. 2,759,515, Nov. 18, 2014, 5 pages, Canada.
Canadian Intellectual Property Office, Requisition by the Examiner for Application No. 2,759,517, Dec. 11, 2014, 5 pages, Canada.
Canadian Intellectual Property Office, Requisition by the Examiner for Application No. 2,759,513, Dec. 9, 2014, 3 pages, Canada.
United States Patent and Trademark Office, Office Action for U.S. Appl. No. 12/980,728, dated Feb. 5, 2015, 38 pages, USA.
United States Patent and Trademark Office, Office Action for U.S. Appl. No. 12/980,747, dated Mar. 3, 2015, 23 pages, USA.
United States Patent and Trademark Office, Office Action for U.S. Appl. No. 12/980,728, dated Aug. 12, 2014, 36 pages, USA.
United States Patent and Trademark Office, Office Action for U.S. Appl. No. 12/980,728, dated Aug. 20, 2014, 30 pages, USA.
United States Patent and Trademark Office, Office Action for U.S. Appl. No. 12/980,747, dated Jul. 24, 2015, 23 pages, U.S.A.
United States Patent and Trademark Office, Office Action for U.S. Appl. No. 12/980,728, dated Sep. 28, 2015, 37 pages, U.S.A.
Canadian Intellectual Propery Office, Requisition by the Examiner for Application No. 2,759,515, Jan. 13, 2016, 4 pages, Canada.
Canadian Intellectual Propery Office, Requisition by the Examiner for Application No. 2,759,513, Feb. 1, 2016, 4 pages, Canada.
Canadian Intellectual Property Office, Requisition by the Examiner for Application No. 2,759,517, Jan. 11, 2016, 5 pages, Canada.
United States Patent and Trademark Office, Office Action for U.S. Appl. No. 12/980,747, dated Dec. 9, 2015, 35 pages, U.S.A.
Canadian Intellectual Property Office, Requisition by the Examiner for Application No. 2,759,517, Nov. 15, 2016, 4 pages, Canada.
United States Patent and Trademark Office, Office Action for U.S. Appl. No. 12/980,747, dated Jul. 5, 2016, 34 pages, U.S.A.
United States Patent and Trademark Office, Office Action for U.S. Appl. No. 12/980,728, dated Jul. 6, 2016, 35 pages, U.S.A.

* cited by examiner

MODES AND WORKFLOWS FOR PROCESSING MEDICATION REQUESTS

BACKGROUND

Today, workflows for processing medication requests have to be manually changed when the need arises. Thus, concepts are needed to allow service providers to define workflows for processing medication requests that can be changed based on factors such as days of the week, time periods within a day, staffing levels, holidays, volume of medication requests, and/or the like.

BRIEF SUMMARY

In general, embodiments of the present invention provide systems, methods, apparatus, and computer program products for processing medication requests.

In accordance with one aspect, a method for processing medication requests is provided. In one embodiment, the method comprises (1) associating a first operational mode with a first workflow of a plurality of workflows for processing medication requests, wherein the first operational mode is initiated by one or more triggers; (2) determining whether one of the one or more triggers of the first operational mode have occurred; (3) after determining that one of the one or more triggers of the first operational mode have occurred, initiating the first operational mode; and (4) processing a plurality of medication requests in accordance with the first workflow.

In accordance with yet another aspect, a computer program product for processing medication requests is provided. The computer program product may comprise at least one computer-readable storage medium having computer-readable program code portions stored therein, the computer-readable program code portions comprising executable portions configured to (1) associate a first operational mode with a first workflow of a plurality of workflows for processing medication requests, wherein the first operational mode is initiated by one or more triggers; (2) determine whether one of the one or more triggers of the first operational mode have occurred; (3) after determining that one of the one or more triggers of the first operational mode have occurred, initiate the first operational mode; and (4) process a plurality of medication requests in accordance with the first workflow.

In accordance with yet another aspect, an apparatus comprising at least one processor and at least one memory including computer program code is provided. In one embodiment, the at least one memory and the computer program code may be configured to, with the processor, cause the apparatus to at least (1) associate a first operational mode with a first workflow of a plurality of workflows for processing medication requests, wherein the first operational mode is initiated by one or more triggers; (2) determine whether one of the one or more triggers of the first operational mode have occurred; (3) after determining that one of the one or more triggers of the first operational mode have occurred, initiate the first operational mode; and (4) process a plurality of medication requests in accordance with the first workflow.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIGS. 3-6 show exemplary input/output that can be produced according to one embodiment of the present invention.

DETAILED DESCRIPTION

Figure 1:
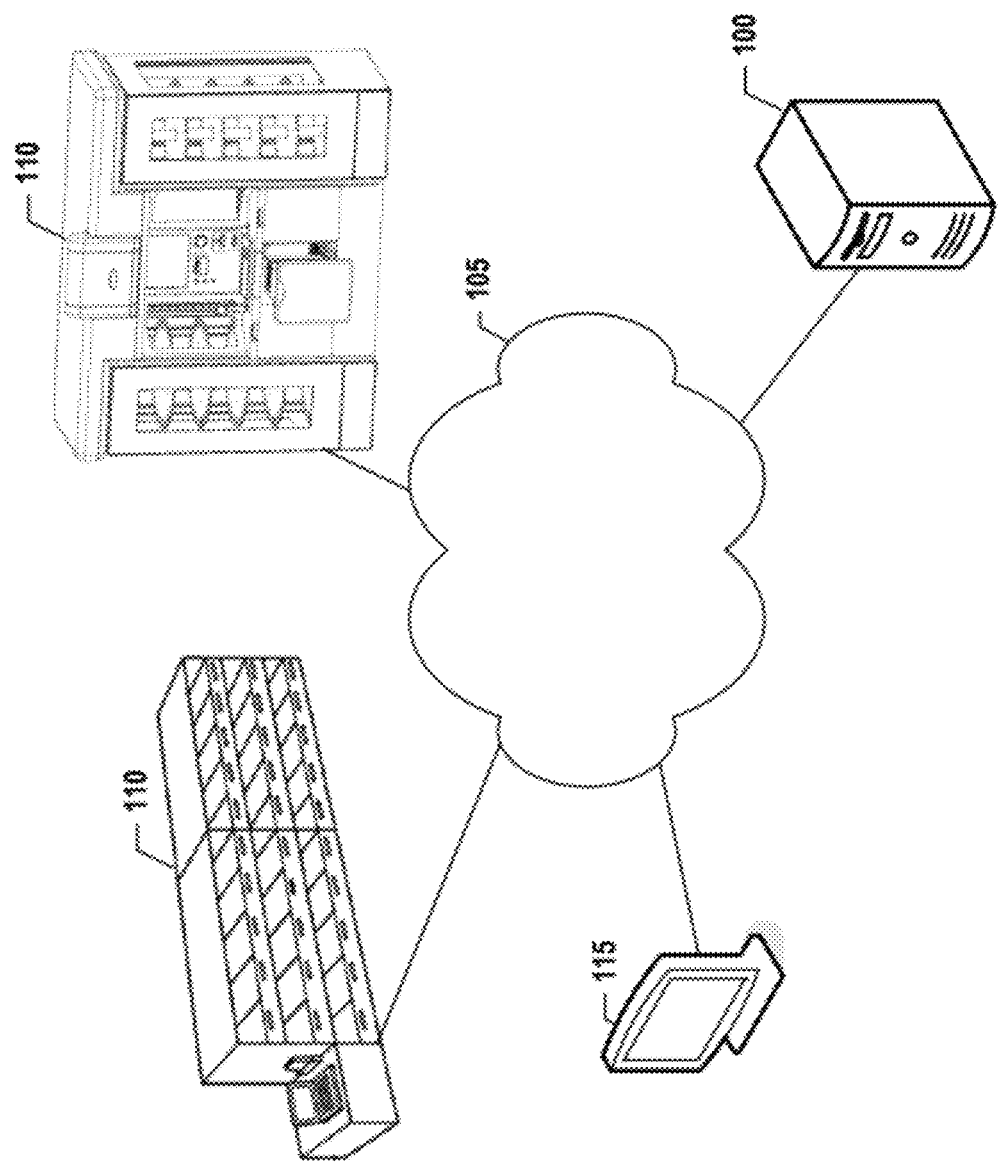
FIG. 1 is an overview of a system that can be used to practice various embodiments of the present invention.

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

I. METHODS, APPARATUS, SYSTEMS, AND COMPUTER PROGRAM PRODUCTS

As should be appreciated, various embodiments may be implemented in various ways, including as methods, apparatus, systems, or computer program products. Accordingly, various embodiments may take the form of an entirely hardware embodiment or an embodiment in which a processor is programmed to perform certain steps. Furthermore, various implementations may take the form of a computer program product on a computer-readable storage medium having computer-readable program instructions embodied in the storage medium. Any suitable computer-readable storage medium may be utilized including hard disks, CD-ROMs, optical storage devices, or magnetic storage devices.

Various embodiments are described below with reference to block diagrams and flowchart illustrations of methods, apparatus, systems, and computer program products. It should be understood that each block of the block diagrams and flowchart illustrations, respectively, may be implemented in part by computer program instructions, e.g., as logical steps or operations executing on a processor in a computing system. These computer program instructions may be loaded onto a computer, such as a special purpose computer or other programmable data processing apparatus to produce a specifically-configured machine, such that the instructions which execute on the computer or other programmable data processing apparatus implement the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the functionality specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide operations for implementing the functions specified in the flowchart block or blocks.

Accordingly, blocks of the block diagrams and flowchart illustrations support various combinations for performing the specified functions, combinations of operations for performing the specified functions and program instructions for performing the specified functions. It should also be understood that each block of the block diagrams and flowchart illustrations, and combinations of blocks in the block diagrams and flowchart illustrations, can be implemented by special purpose hardware-based computer systems that perform the specified functions or operations, or combinations of special purpose hardware and computer instructions.

II. GENERAL OVERVIEW

In general, according to various embodiments of the present invention, methods, apparatus, systems, and computer program products are provided for processing medication requests. In one embodiment, a server can receive input defining operational modes to be used for processing medication requests. For example, the server may receive input defining (a) operational modes, such as operational modes to be used Monday through Friday from 8:00 am to 10:00 am and 1:00 pm to 5:00 pm, and (b) triggers for initiating the operational modes, such as days of the week and times of the day. The server can also receive input defining workflows for processing medication requests. Workflows may be used to, for example, identify which devices should be used to fill medication requests and the order and manner in which the requests should be processed.

In one embodiment, workflows can then be associated with operational modes. After workflows are associated with operational modes, the server can monitor the triggers for initiating the operational modes. Once a trigger occurs, the server can initiate the appropriate operational mode and process medication requests in accordance with the associated workflow or workflows.

III. EXEMPLARY SYSTEM ARCHITECTURE

FIG. 1 provides an illustration of a system that can be used in conjunction with various embodiments of the present invention. As shown in FIG. 1, the system may include one or more medication servers 100, one or more networks 105, one or more medication filling devices 110, and one or more clients 115. Each of the components of the system may be in electronic communication with, for example, one another over the same or different wireless or wired networks including, for example, a wired or wireless Personal Area Network ("PAN"), Local Area Network ("LAN"), Metropolitan Area Network ("MAN"), Wide Area Network ("WAN"), or the like. Additionally, while FIG. 1 illustrates certain system entities as separate, standalone entities, the various embodiments are not limited to this particular architecture.

1. Exemplary Medication Server

Figure 2:
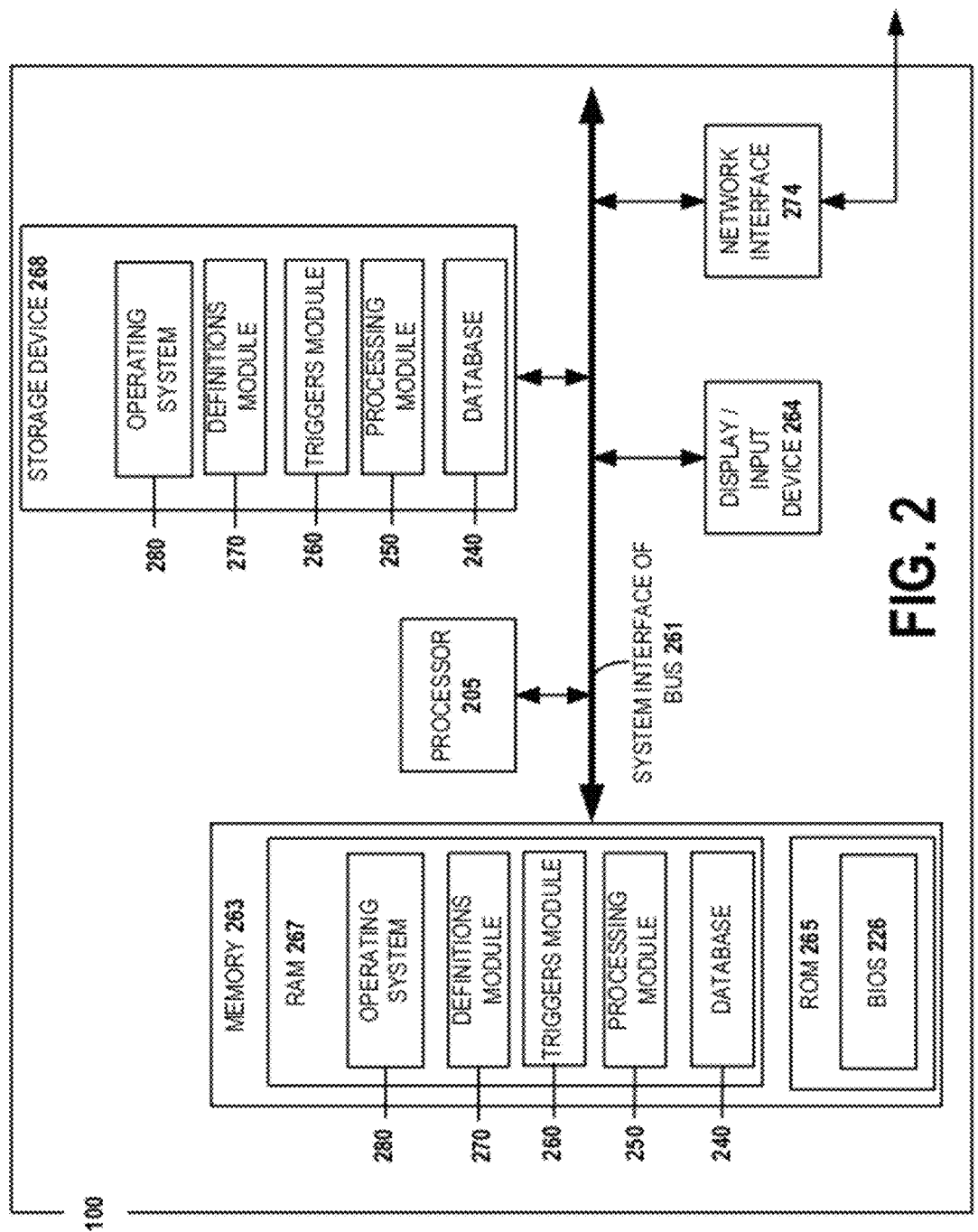
FIG. 2 is an illustrative schematic diagram of a medication server according to one embodiment of the present invention.

FIG. 2 provides a schematic of a medication server 100 according to one embodiment of the present invention. In general, the term "server" may refer to, for example, any computer, computing device, mobile phone, desktop, notebook or laptop, distributed system, server, blade, gateway, switch, processing device, or combination of processing devices adapted to perform the functions described herein.

As will be understood from this figure, in one embodiment, the medication server 100 includes a processor 205 that communicates with other elements within the medication server 100 via a system interface or bus 261. The processor 205 may be embodied in a number of different ways. For example, the processor 205 may be embodied as a processing element, a coprocessor, a controller or various other processing devices including integrated circuits such as, for example, an application specific integrated circuit ("ASIC"), a field programmable gate array ("FPGA"), a hardware accelerator, or the like.

In an exemplary embodiment, the processor 205 may be configured to execute instructions stored in the device memory or otherwise accessible to the processor 205. As such, whether configured by hardware or software methods, or by a combination thereof, the processor 205 may represent an entity capable of performing operations according to embodiments of the present invention when configured accordingly. A display device/input device 264 for receiving and displaying data may also be included in the medication server 100. This display device/input device 264 may be, for example, a keyboard or pointing device that is used in combination with a monitor. The medication server 100 may further include transitory and non-transitory memory 263, which may include both random access memory ("RAM") 267 and read only memory ("ROM") 265. The medication server's ROM 265 may be used to store a basic input/output system ("BIOS") 226 containing the basic routines that help to transfer information to the different elements within the medication server 100.

In addition, in one embodiment, the medication server 100 may include at least one storage device 268, such as a hard disk drive, a CD drive, and/or an optical disk drive for storing information on various computer-readable media. The storage device(s) 268 and its associated computer-readable media may provide nonvolatile storage. The computer-readable media described above could be replaced by any other type of computer-readable media, such as embedded or removable multimedia memory cards ("MMCs"), secure digital ("SD") memory cards, Memory Sticks, electrically erasable programmable read-only memory ("EEPROM"), flash memory, hard disk, or the like. Additionally, each of these storage devices 268 may be connected to the system bus 261 by an appropriate interface.

Furthermore, a number of program modules may be stored by the various storage devices 268 and/or within RAM 267. Such program modules may include an operating system 280, a definitions module 270, a triggers module 260, and a processing module 250. As discussed in more detail below, these modules may control certain aspects of the operation of the medication server 100 with the assistance of the processor 205 and operating system 280—although their functionality need not be modularized. In addition to the program modules, the medication server 100 may store or be in communication with one or more databases (e.g., database 240).

Also located within the medication server 100, in one embodiment, is a network interface 274 for interfacing with various computing entities. This communication may be via the same or different wired or wireless networks (or a combination of wired and wireless networks), as discussed above. For instance, the communication may be executed using a wired data transmission protocol, such as fiber distributed data interface ("FDDI"), digital subscriber line ("DSL"), Ethernet, asynchronous transfer mode ("ATM"), frame relay, data over cable service interface specification ("DOCSIS"), or any other wired transmission protocol.

Similarly, the medication server 100 may be configured to communicate via wireless external communication networks using any of a variety of protocols, such as 802.11, general packet radio service ("GPRS"), wideband code division multiple access ("W-CDMA"), Long Term Evolution ("LTE"), IEEE 802.11 ("Wi-Fi"), 802.16 ("WiMAX"), ultra wideband ("UWB"), and/or any other wireless protocol.

It will be appreciated that one or more of the medication server's 100 components may be located remotely from other medication server 100 components. Furthermore, one or more of the components may be combined and additional components performing functions described herein may be included in the medication server 100.

2. Exemplary Medication Filling Devices/Systems

As shown in FIG. 1, the system may include one or more medication filling devices 110. A medication filling device 110 may be a device, apparatus, robot, system, computer, and/or the like that can be used in filling medication requests. For example, a medication filling device 110 may be a ROBOT-Rx® automated medication dispensing system, MedCarousel® system, MedShelf system, IntelliShelf-Rx® system, PROmanager-Rx™ pharmacy automation system, PACMED™ high-speed packager, Satellite Replenishment system, Fulfill-Rx<sup>SM</sup> solution, and/or the like. Thus, as will be recognized, medication filling devices 110 may operated automatically, semi-automatically, and/or manually and include various components such as (1) processing elements, (2) memory, (3) network interfaces, (4) transceivers, (5) display devices/input devices, input and/or (6) various other components.

By way of example, in one embodiment, a pharmacist or pharmacy technician may use a MedCarousel® system or MedShelf system to manually pick medications to fill medication requests. For example, the MedShelf system may receive (from the medication server 100) and display medication requests that are assigned to a particular medication filling device 110, pharmacist, and/or pharmacy technician for filling. Using the MedShelf system, the pharmacist or pharmacy technician can manually fill the medication requests and enter input via the MedShelf system indicating that the medication requests have been filled.

In another embodiment, automated systems may facilitate the filling of medication requests. For example, ROBOT-Rx® is a stationary robotic system that automates the medication storing, dispensing, returning, restocking, and crediting process by using various technologies. Operatively, ROBOT-Rx® can receive medication requests from the medication server 100. At the appropriate time, ROBOT-Rx® can guide a picking mechanism to select the desired medications and deposit them in, for example, specific boxes or containers to fill a particular medication request. In response to (e.g., after) filling a medication request, ROBOT-Rx® can transmit a message to the medication server 100, for example, indicating that the medication request has been filled.

As will be recognized, a variety of approaches and techniques may be used for filling medication requests. Accordingly, the foregoing examples are provided for illustrative purposes only and should not be taken in any way as limiting embodiments of the present invention to the examples provided.

3. Exemplary Clients

As shown in FIG. 1, a system according to an exemplary embodiment may include one or more clients 115. In one embodiment, clients 115 may include components such as (1) processing elements, (2) memory, (3) network interfaces, (4) transceivers, and/or (5) various other components. Via such components, the clients 115 may display/present information, for example, related to medication requests, workflows, and/or operational modes. Moreover, the clients 115 may be used to define one or more operational modes, define one or more workflows, associate workflows with operational modes, monitor medication request processing, and/or the like.

IV. EXEMPLARY SYSTEM OPERATION

Figure 5:
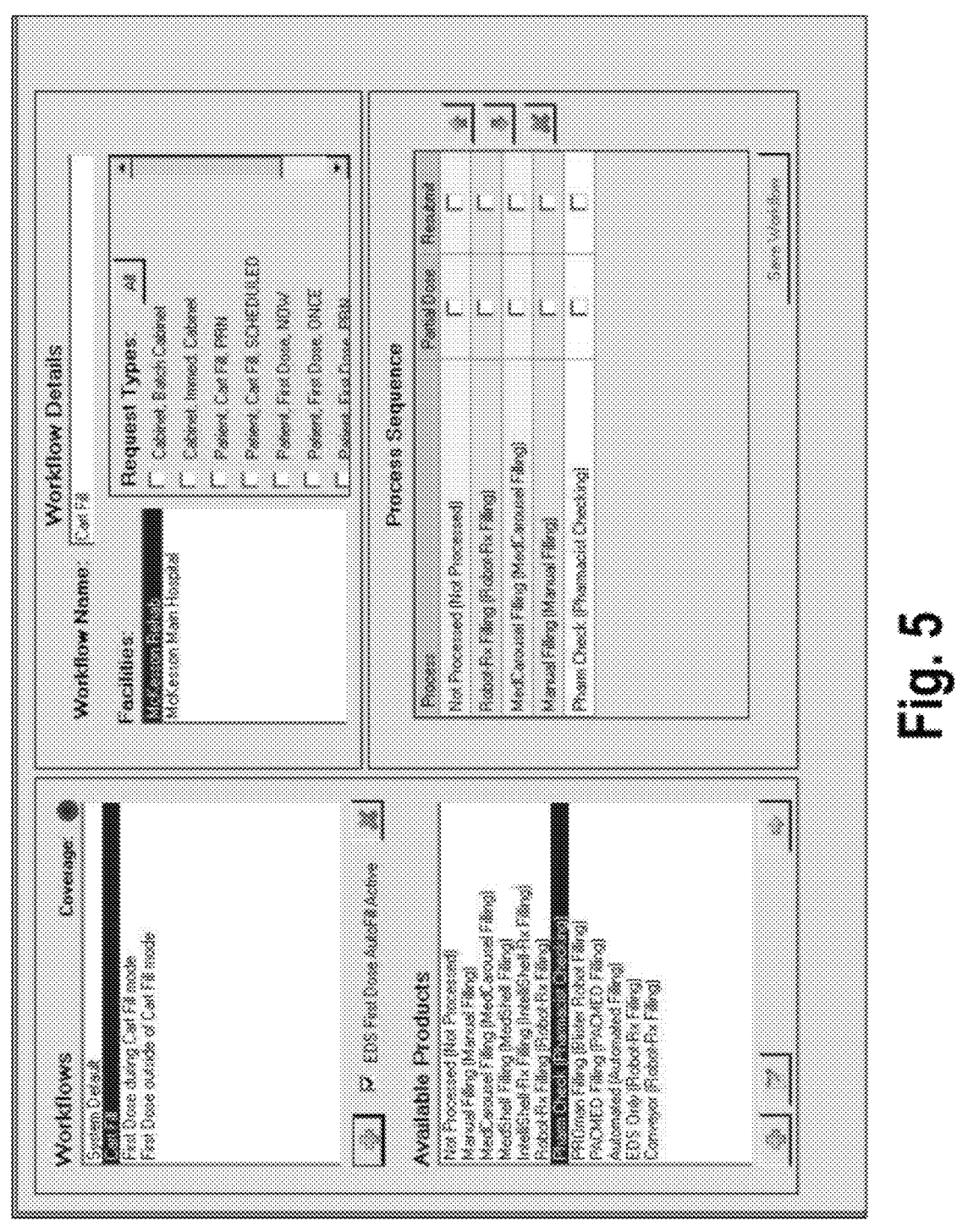
Figure 6:
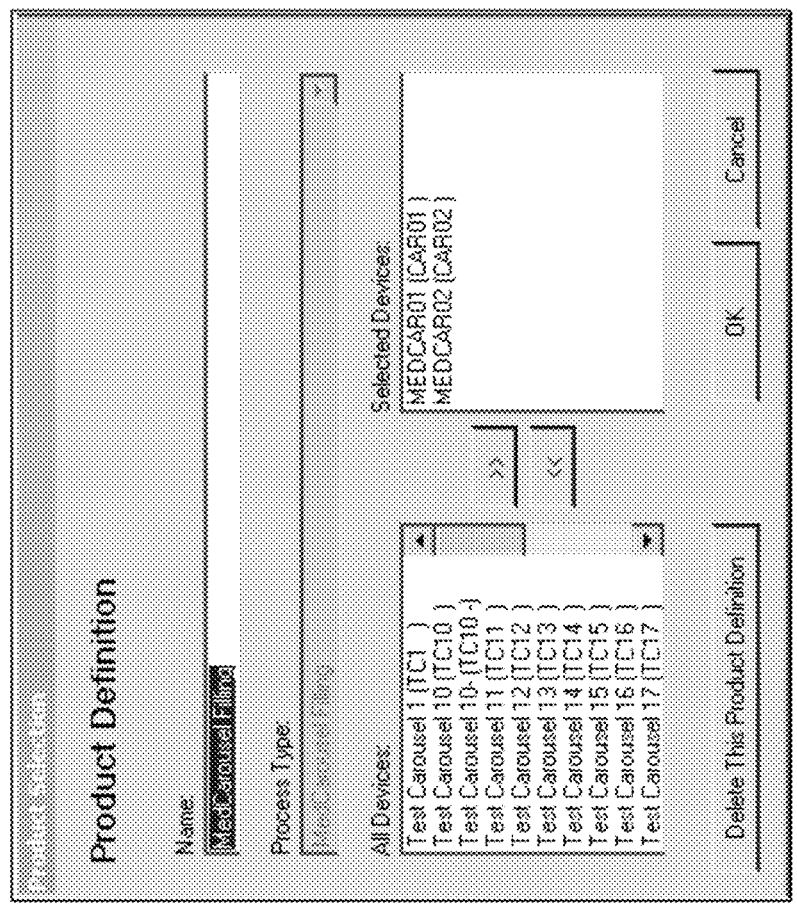
Figure 7:
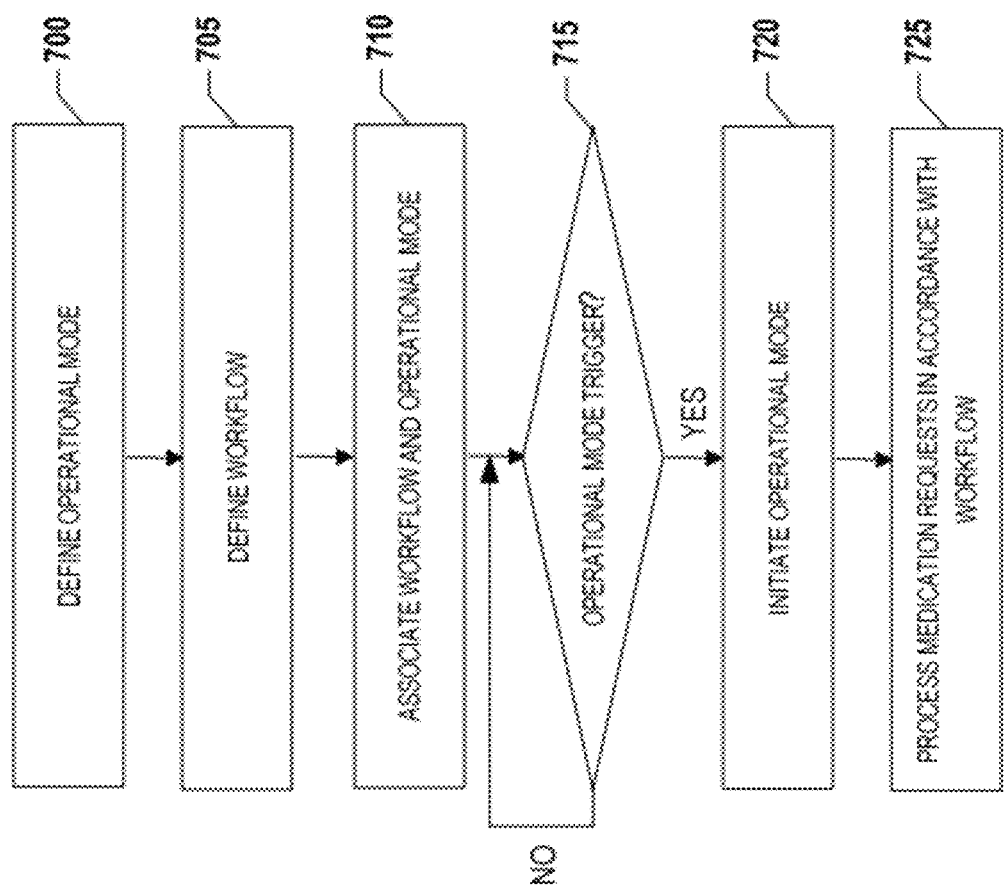
FIG. 7 is a flowchart illustrating operations and processes that can be used in accordance with various embodiments of the present invention.

Reference will now be made to FIGS. 3-7. FIGS. 3-6 show exemplary input/output for processing medication requests. FIG. 7 is a flowchart illustrating operations and processes that can be used for processing medication requests.

1. Exemplary Medication Requests

Patients undergoing medical care or treatment are often placed on medication treatment plans that require them to take one or more doses of medication for a period of time. For example, some medications may require administration at certain times of the day (e.g., after meals) and/or at intervals of one or more hours each day. When a medical provider prescribes medication to a patient, the medical provider can transmit medication requests, for example, to a pharmacy (e.g., medication server 100) for filling. Thus, such medication requests can be routinely, periodically, and/or continuously received by the medication server 100 for filling from a variety of medical providers (e.g., doctors, hospitals, other pharmacies, departments or storage locations within health care facilities, and/or the like).

Medication requests may be used to request certain quantities of one or more medications. To assist in processing medication requests, each medication request may include information, such as patient name, patient birth date, patient identification number, patient insurance information, patient allergies, patient location, medication request type, medication request priority, medication filling commit time, types of medications requested, quantities of each medication requested, and/or the like.

Medication requests may be used, for example, to fill prescriptions of patients or to transfer inventory from one location to another. For instance, the medication request type may be used to indicate that the medication request is a patient request or an inventory request. In one embodiment, patient requests may be "cart-fill" requests, "first-dose" requests, and/or the like. A cart-fill medication request may be used to indicate that the medication request is for a patient but is to be filled as part of a batch process of medication requests that, for example, are delivered daily to a hospital, unit in a hospital, and/or health care facility. A first-dose medication request may be used to indicate medication requests that are needed promptly, such as for newly admitted patients or when there is a change to a medication that was cart-filled.

In one embodiment, inventory requests may be "cabinet refill" requests, "inventory transfer" requests, "packaging" requests, and/or the like. A cabinet refill request may be used to indicate that the medication request is to refill a medication cabinet, for example, located at a nursing station within a health care facility. For example, when medication levels in a medication cabinet in a cardiovascular wing are low, a cabinet refill request may be generated to refill one or more medications in the cabinet. An inventory transfer request may be used to provide items to a storage location (e.g., restocking room), and a packaging request may be used to initiate the packaging of medications into unit dose packages. As will be recognized, a variety of other approaches and techniques can be used to adapt to various needs and circumstances.

As will be recognized, a variety of medication request types, approaches, and techniques can be used for receiving and identifying medication requests. Further, in response to (e.g., after) receiving medication requests, the medication server 100 can process the medication requests for filling in accordance with one or more operational modes and/or one or more workflows.

2. Exemplary Operational Modes

In one embodiment, pharmacies may operate differently on certain days, at different times of the day, and/or in response to different circumstances. For example, a pharmacy may have different workflows (e.g., steps or rules) for processing medication requests at certain times, such as on weekday mornings, weekday afternoons, weekday evenings (e.g., manual medication requests may be routed to several pharmacy technicians for filling in parallel), weekends (e.g., manual medication requests may be routed to a single pharmacy technician), and/or holidays. Similarly, a pharmacy may have workflows for processing medication requests in response to certain triggers/parameters, such as when the volume of medication requests waiting to be filled surpasses a predetermined threshold or the frequency at which medication requests are received surpasses a predetermined threshold. Still further, a pharmacy may have workflows for processing medication requests based on device availability. For example, if a Robot-Rx® conveyor is down due to hardware problems, the pharmacy may want that event to trigger the use of a different workflow. Such triggers/parameters of operational modes can be used to automatically, semi-automatically, and/or manually initiate the use of the specific operational modes.

Figure 3:
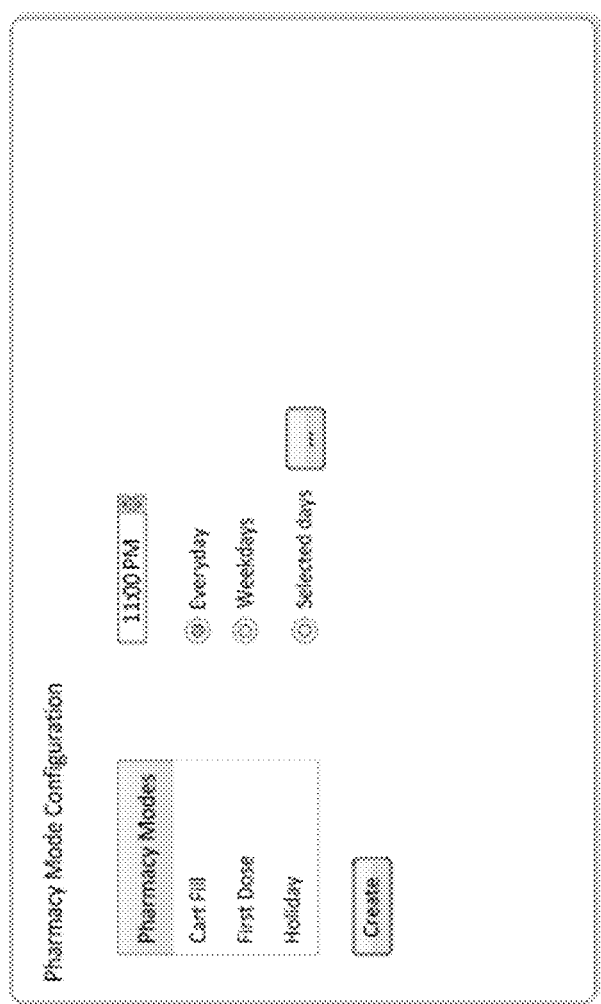

To that end, as indicated in Block 700 of FIG. 7 and shown in FIG. 3, the medication server 100 can receive input (e.g., via a user operating a client 115) defining one or more operational modes to be used for processing medication requests (e.g., via the definitions module 270). For example, the medication server 100 may receive input (e.g., via a user operating a client 115) defining a first operational mode to be used Monday through Friday from 8:00 am to 10:00 am and 1:00 pm to 5:00 pm. In this example, the one or more triggers/parameters for initiating the first operational mode may be (1) Monday, Tuesday, Wednesday, Thursday, and Friday at 8:00 am and (2) Monday, Tuesday, Wednesday, Thursday, and Friday at 1:00 pm.

As will be recognized, various operational modes may be defined to adapt to a variety of needs and circumstances. For example, in one embodiment, the medication server 100 can receive input (e.g., via a user operating a client 115) defining a second operational mode to be used Monday through Friday from 10:00 am to 1:00 pm. In another embodiment, a third operational mode can be defined to be used all day on Saturdays and Sundays. In yet another embodiment, a fourth operational mode can be defined to be used on holidays. In still another embodiment, a fifth operational mode can be defined to be used Monday through Friday from 5:00 pm to 8:00 am. In another embodiment, a sixth operational mode can be defined to be used, for example, when 65 or more medication requests are received by the medication server 100 within a 30 minute period of time. In another embodiment, the medication server 100 can receive input (e.g., via a user operating a client 115) defining a seventh operational mode to be used, for example, when there are 150 or more first-dose medication requests waiting to be filled. In various embodiments, the operational modes and their corresponding triggers/parameters can allow pharmacies and/or other medical providers to customize operational modes and workflows in response to, for example, different days of the week, time periods within a day, staffing levels, holidays, volumes of medication requests waiting to be filled, frequencies at which medication requests are received, and/or the like. The various operational modes can then be stored by the medication server 100.

In one embodiment, as indicated in Block 715 of FIG. 7, the medication sever 100 can routinely, periodically, and/or continuously monitor various triggers/parameters to determine whether one or more of the triggers/parameters associated with the operational modes have occurred (e.g., via the triggers module 260). In response to (e.g., after) determining that one or more triggers/parameters of, for example, the first operational mode have occurred, the medication server 100 can be used to automatically, semi-automatically, and/or manually initiate the first operational mode (Block 720 of FIG. 7). For example, in response to (e.g., after) determining that one or more triggers/parameters of an operational mode have occurred, the medication server 100 can automatically initiate the mode (and its corresponding workflows) without any user interaction. Similarly, the medication server 100 can semi-automatically initiate the mode (and its corresponding workflows), for example, by displaying a screen prompt indicating that the mode (and its corresponding workflows) will be initiated within a predetermined period of time (e.g., 120 seconds) unless the user takes certain actions. Still further, the medication server 100 can be used to manually initiate the mode, for example, by displaying a screen prompt indicating that the triggers/parameters have occurred but that the mode (and its corresponding workflows) will only be initiated if the user takes certain actions.

In one embodiment, when a plurality of operational modes have been defined, the medication sever 100 can also be used to automatically, semi-automatically, and/or manually resolve conflicts between operational modes and/or workflows. For example, a holiday operational mode may be defined to have priority over a regularly-scheduled weekday operational mode. Thus, in an instance in which the triggers/parameters for both operational modes have occurred, the medication sever 100 can be used to determine which operational mode should actually be initiated. As will be recognized, a variety of approaches and techniques can be used to define operational modes, initiate operational modes, and/or resolve conflicts.

3. Exemplary Workflows

In one embodiment, once an operational mode is initiated, medication requests can be processed in accordance with the workflows associated with the operational mode. A workflow may define, for example, how medication requests (or certain types of medication requests) should be processed. For instance, a workflow (e.g., patient workflows and inventory workflows) may be used to identify which medication filling devices 110 should be used with the workflow (e.g., any number of devices can be grouped). The workflow may also define the types of medication requests that should be processed and the order and manner in which the medication requests should proceed (if necessary) to the different medication filling devices 110. The workflow may also define a variety of other processing parameters, such as the order in which medication requests for certain facilities or patients should be processed. For example, medication requests from a main hospital may have priority over medication requests from a rehab center. As will be recognized, a variety of processing parameters can be defined to adapt to various needs and circumstances.

Figure 4:
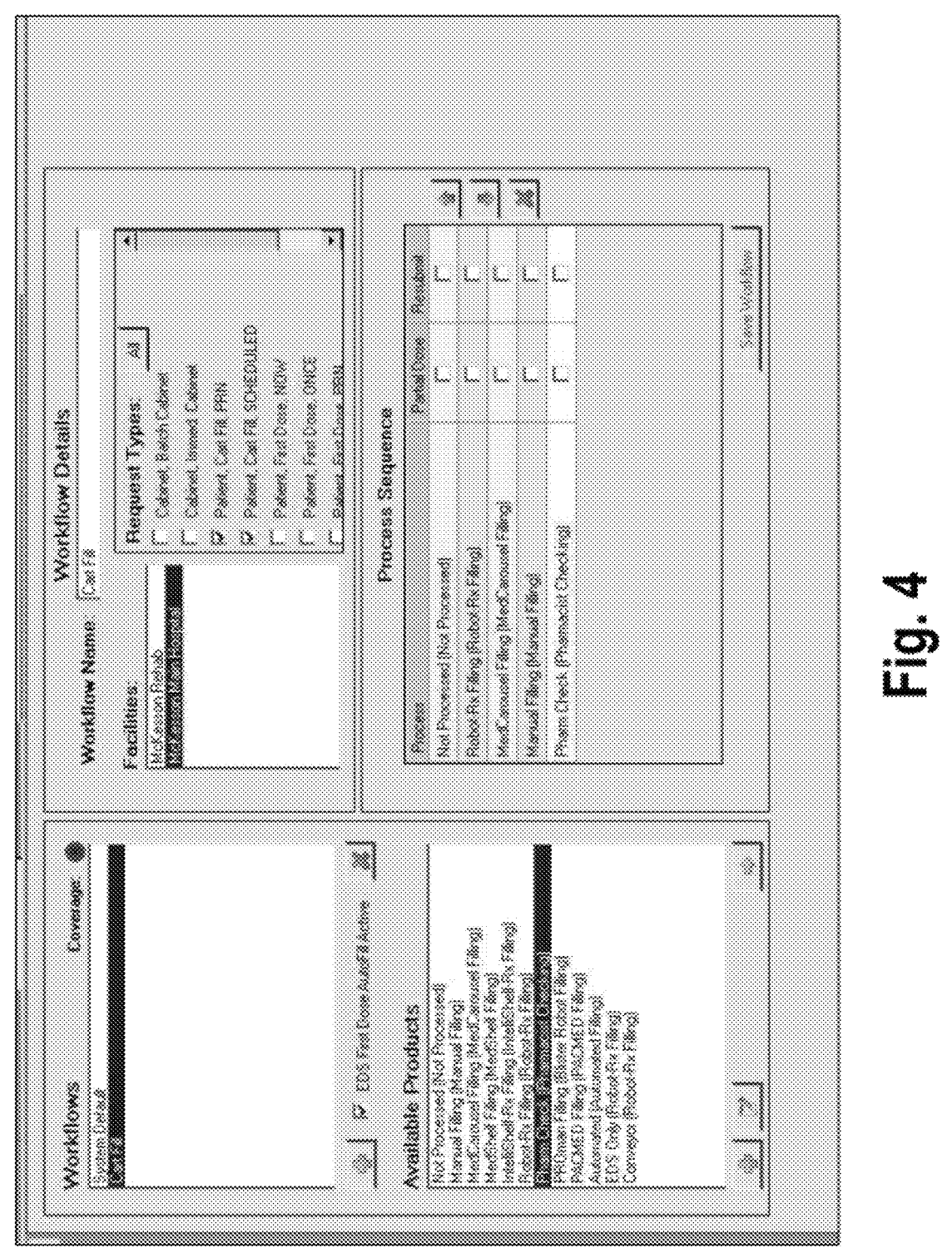

To that end, as indicated in Block 705 of FIG. 7 and shown in FIGS. 4-6, the medication server 100 can receive input (e.g., via a user operating a client 115) defining a plurality of workflows for processing medication requests (e.g., via the definitions module 270) and store it. For example, the medication server 100 may receive input (e.g., via a user operating a client 115) defining a first-dose workflow (e.g., a first workflow for processing first-dose medication requests). The first workflow may indicate that only first-dose medication requests should be processed in accordance with the first workflow. The first workflow may also indicate that only the ROBOT-Rx® and MedCarousel® devices/systems should be used with the workflow. And finally, the first workflow may define how the first-dose medication requests should be processed. For instance, the first workflow may define that first-dose medication requests should be first routed to the ROBOT-Rx® device for filling if the ROBOT-Rx® device is capable of dispensing at least one of the requested medications. The first workflow may also indicate that a medication request that is only partially filled by ROBOT-Rx® should be routed to the MedCarousel® for completion.

In another embodiment, as indicated in Block 705 of FIG. 7 and shown in FIGS. 4-6, the medication server 100 can receive input (e.g., via a user operating a client 115) defining a cart-fill workflow (e.g., a second workflow for processing cart-fill medication requests in batch) and store them. The second workflow may indicate that only cart-fill medication requests should be processed in accordance with the second workflow. The second workflow may also indicate that only the ROBOT-Rx® devices should be used with the workflow and that that first-dose medication requests should be picked manually elsewhere and/or using other medication filling devices. The second workflow may also define how the cart-fill medication requests should be processed. For instance, the second workflow may define that cart-fill medication requests are first to be routed to a primary ROBOT-Rx® for filling until the medication requests routed to the primary ROBOT-Rx® device meet a predetermined threshold at which time medication requests can be routed to one or more secondary ROBOT-Rx® devices. Such processing may continue until the medication requests for the primary ROBOT-Rx® device fall below the predetermined threshold.

In one embodiment, the workflows can also be used to define other processing steps/procedures for filling medication requests. For example, workflows can define how filled and partially-filled medication requests should be checked for accuracy. The workflows can also define various entry states and possible exit states for each workflow. The workflows may also define how medication requests should be distributed for checking among, for example, pharmacists or pharmacy technicians. For example, a workflow may indicate that medication requests are to be routed to a primary pharmacy technician until the medication requests routed to the primary pharmacy technician meet a predetermined threshold at which point medication requests should be routed to a pharmacist or one or more secondary pharmacy technicians.

As indicated in Block 710 of FIG. 7, in one embodiment, after one or more workflows have been defined, workflows can be associated with operational modes. For example, the first operational mode may be associated (e.g., via a user operating a client 115) with one or more first-dose workflows, one or more cart-fill workflows, one or more cabinet refill workflows, one or more inventory transfer workflows, one or more packaging workflows, and/or one or more other workflows. Similarly, the second, third, fourth, fifth, sixth, and seventh operational modes, for instance, may also be associated with one or more workflows for processing medication requests.

In various embodiments, these concepts may allow pharmacies, for example, to configure their medication filling devices 110 in a manner that will efficiently pick the medications to fill the medication requests sent to the pharmacy. Thus, as will be recognized, a variety of workflows, approaches, and techniques can be used for processing medication requests. Thus, the foregoing examples are provided for illustrative purposes only and should not be taken in any way as limiting embodiments of the present invention to the examples provided.

4. Exemplary Processing of Medication Requests

As described, the medication server 100 can receive medication requests for filling on a routine, periodic, and/or continuous basis from a variety of medical providers. The medication sever 100 can also routinely, periodically, and/or continuously monitor various triggers/parameters to determine whether one or more of the triggers/parameters associated with the operational modes have occurred (Block 715 of FIG. 7). In response to (e.g., after) determining that one or more triggers/parameters of an operational mode have occurred, the medication server 100 can be used to automatically, semi-automatically, and/or manually initiate the appropriate operational mode (Block 720 of FIG. 7). Initiating the appropriate operational mode includes initiating the workflows for processing medication requests that are associated with that operational mode (Block 725 of FIG. 7).

In one embodiment, after initiating the appropriate operational mode, the medication server 100 can process the medication requests in accordance with workflows associated with that operational mode (e.g., via the processing module 250). For example, to process a first-dose medication request in accordance with a first-dose workflow associated with the current operational mode, the medication server 100 may transmit the first-dose medication request to a ROBOT-Rx® device to fill (or at least partially fill) the medication request. A pharmacy technician can view the medication request via a display (e.g., a dashboard) disposed on or adjacent the ROBOT-Rx® device. The pharmacy technician can then print out a label and affix it to a bin (and/or box or bag) and place the bin on a conveyer, for example, for processing. When the bin is moved into the scan position, the ROBOT-Rx® device can scan the label and pick the medications associated with the medication request. That is, the ROBOT-Rx® can guide a picking mechanism to select the desired medications and deposit them in the bin and transmit a message to the medication server 100 indicating which medications were picked. If additional medications are required to complete filling the medication request, the medication server 100 can then route the medication request in accordance with the workflow to the appropriate device (e.g., MedCarousel®) to be picked. For example, the medication server 100 may transmit the first-dose medication request to a MedCarousel® system to complete the medication request. Using the MedCarousel® system, a pharmacist or a pharmacy technician can view (e.g., via a display) the remaining medications that are necessary to fill the first-dose medication request. After the pharmacist or pharmacy technician picks the remaining medications, the medications picked to fill the medication request may be checked for accuracy and packaged in accordance with the workflow. If accurate and completely filled, the pharmacist or pharmacy technician can enter input via the MedCarousel® system indicating that the first-dose medication request has been filled. The input can then be transmitted to the medication server 100, which can update its records to reflect the filling.

In one embodiment, to process cart-fill medication requests in accordance with a cart-fill workflow associated with the current operational mode, the medication server 100 may transmit the cart-fill medication requests to a primary ROBOT-Rx® device to fill (or at least partially fill) the medication requests. A pharmacy technician can view the medication requests via a display (e.g., a dashboard) disposed on or adjacent the primary ROBOT-Rx® device. The pharmacy technician can then print out labels and affix them to bins (and/or boxes or bags) and place the bins on a conveyer, for example, for processing. Each time the bin is moved into the scan position, the primary ROBOT-Rx® device can scan the corresponding label and pick the medications associated with the medication request. After the medications associated with the medication request have been picked, the medications may be checked for accuracy and packaged in accordance with the workflow. If accurate and completely filled, the primary ROBOT-Rx® (or other appropriate device) can transmit an indication to the medication server 100 that the cart-fill medication request has been filled. The medication server 100 can then update its records to reflect the filling.

As will be recognized, the preceding examples briefly describe particular embodiments for filling medication requests. The described examples are provided only for illustrative purposes and should not be taken in any way as limiting embodiments of the present invention to the examples provided. Thus, as will be recognized, a variety of other approaches and techniques may be used.

V. CONCLUSION

And as will be recognized, many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for processing medication requests, the method comprising:
electronically associating, via one or more processors, a first operational mode with a first workflow of a plurality of workflows for automatically processing medication requests, (a) the first operational mode automatically initiated by the detection of one or more triggers, (b) each of the plurality of workflows identifying (i) one or more automated medication filling devices to be used for filling medication requests in accordance with the corresponding workflow and (ii) one or more types of medication requests to be filled in accordance with the corresponding workflow, and (c) the one or more triggers selected from the group consisting of a day of the week, a time of day, a number of medication requests received over a time period, and a frequency of medication requests received over a time period;
electronically storing, via one or more processors, the first operational mode in association with the first workflow;
automatically determining, via the one or more processors, whether one of the one or more triggers of the first operational mode has occurred;
responsive to determining that one of the one or more triggers of the first operational mode has occurred, automatically initiating, via the one or more processors, the first operational mode and the first workflow for processing medication requests;
identifying, via the one or more processors, (a) the one or more automated medication filling devices to be used for automatically filling medication requests in accordance with the first workflow of the first operational mode and (b) the one or more types of medication requests to be filled in accordance with the first workflow of the first operational mode;
electronically receiving, via the one or more processors, data for a plurality of medication requests;
automatically processing, via the one or more processors, each of the plurality of medication requests using the one or more automated medication filling devices to be used for filling medication requests in accordance with the first workflow of the first operational mode; and
automatically filling the medication requests of the plurality of medication requests that are of the one or more types of medication requests to be filled in accordance with the first workflow of the first operational mode using the one or more automated medication filling devices, wherein the filling of the medication requests of the plurality of medication requests is in accordance with the first workflow of the first operational mode.

2. The method of claim 1 further comprising:
receiving input defining the first operational mode that is initiated by the one or more triggers; and
receiving input defining the plurality of workflows for processing medication requests.

3. The method of claim 2 further comprising:
associating, via the one or more processors, the first operational mode with a second workflow of the plurality of workflows; and
processing, via the one or more processors, the plurality of medication requests in accordance with the first and second workflows.

4. The method of claim 3 further comprising:
receiving input defining a second operational mode that is initiated by the detection of one or more triggers;
associating, via the one or more processors, the second operational mode with a third workflow of the plurality of workflows;
determining, via the one or more processors, whether one of the one or more triggers of the second operational mode has occurred;
after determining that one of the one or more triggers of the second operational mode has occurred, initiating the second operational mode; and
processing, via the one or more processors, the plurality of medication requests in accordance with the third workflow.

5. The method of claim 4 further comprising:
associating, via the one or more processors, a fourth workflow of the plurality of workflows for processing medication requests with the second operational mode; and processing, via the one or more processors, the plurality of medication requests in accordance with the third and fourth workflows.

6. The method of claim 1, wherein each of the plurality of workflows for processing medication requests comprises (a) a patient workflow or (b) an inventory workflow.

7. A computer program product for processing medication requests, the computer program product comprising at least one non-transitory computer-readable storage medium having computer-readable program code portions stored therein, the computer-readable program code portions comprising:
an executable portion configured to electronically associate a first operational mode with a first workflow of a plurality of workflows for automatically processing medication requests, (a) the first operational mode automatically initiated by the detection of one or more triggers, (b) each of the plurality of workflows identifying (i) one or more automated medication filling devices to be used for filling medication requests in accordance with the corresponding workflow and (ii) one or more types of medication requests to be filled in accordance with the corresponding workflow, and (c) the one or more triggers selected from the group consisting of a day of the week, a time of day, a number of medication requests received over a time period, and a frequency of medication requests received over a time period;
an executable portion configured to electronically store the first operational mode in association with the first workflow;
an executable portion configured to automatically determine whether one of the one or more triggers of the first operational mode has occurred;
an executable portion configured to, responsive to determining that one of the one or more triggers of the first operational mode has occurred, automatically initiate the first operational mode and the first workflow for processing medication requests;
an executable portion configured to identify (a) the one or more automated medication filling devices to be used for automatically filling medication requests in accordance with the first workflow of the first operational mode and (b) the one or more types of medication requests to be filled in accordance with the first workflow of the first operational mode;
an executable portion configured to receive data for a plurality of medication requests;
an executable portion configured to automatically process each of the plurality of medication requests using the one or more automated medication filling devices to be used for filling medication requests in accordance with the first workflow of the first operational mode; and
an executable portion configured to automatically fill the medication requests of the plurality of medication requests that are of the one or more types of medication requests to be filled in accordance with the first workflow of the first operational mode using the one or more automated medication filling devices, wherein the filling of the medication requests of the plurality of medication requests is in accordance with the first workflow of the first operational mode.

8. The computer program product of claim 7 further comprising:
an executable portion configured to receive input defining the first operational mode that is initiated by the one or more triggers; and
an executable portion configured to receive input defining the plurality of workflows for processing medication requests.

9. The computer program product of claim 8 further comprising:
an executable portion configured to receive the plurality of medication requests; and
an executable portion configured to associate the first operational mode with a second workflow of the plurality of workflows; and
an executable portion configured to process the plurality of medication requests in accordance with the first and second workflows.

10. The computer program product of claim 9 further comprising:
an executable portion configured to receive input defining a second operational mode that is initiated by one or more triggers;
an executable portion configured to associate the second operational mode with a third workflow of the plurality of workflows;
an executable portion configured to determine whether one of the one or more triggers of the second operational mode has occurred;
an executable portion configured to, after determining that one of the one or more triggers of the second operational mode has occurred, initiate the second operational mode; and
an executable portion configured to process the plurality of medication requests in accordance with the third workflow.

11. The computer program product of claim 10 further comprising:
an executable portion configured to associate a fourth workflow of the plurality of workflows for processing medication requests with the second operational mode; and
an executable portion configured to process the plurality of medication requests in accordance with the third and fourth workflows.

12. The computer program product of claim 7, wherein each of the plurality of workflows for processing medication requests comprises (a) a patient workflow or (b) an inventory workflow.

13. An apparatus comprising at least one processor and at least one memory including computer program code, the at least one memory and the computer program code configured to, with the processor, cause the apparatus to at least:
electronically associate a first operational mode with a first workflow of a plurality of workflows for automatically processing medication requests, (a) the first operational mode automatically initiated by the detection of one or more triggers, (b) each of the plurality of workflows identifying (i) one or more automated medication filling devices to be used for filling medication requests in accordance with the corresponding workflow and (ii) one or more types of medication requests to be filled in accordance with the corresponding workflow, and (c) the one or more triggers selected from the group consisting of a day of the week, a time of day, a number of medication requests received over a time period, and a frequency of medication requests received over a time period;
electronically store the first operational mode in association with the first workflow;
automatically determine whether one of the one or more triggers of the first operational mode has occurred;

responsive to determining that one of the one or more triggers of the first operational mode has occurred, automatically initiate the first operational mode and the first workflow for processing medication requests;

identify (a) the one or more automated medication filling devices to be used for automatically filling medication requests in accordance with the first workflow of the first operational mode and (b) the one or more types of medication requests to be filled in accordance with the first workflow of the first operational mode;

receive data for a plurality of medication requests;

automatically process each of the plurality of medication requests using the one or more automated medication filling devices to be used for filling medication requests in accordance with the first workflow of the first operational mode; and automatically fill the medication requests of the plurality of medication requests that are of the one or more types of medication requests to be filled in accordance with the first workflow of the first operational mode using the one or more automated medication filling devices, wherein the filling of the medication requests of the plurality of medication requests is in accordance with the first workflow of the first operational mode.

14. The apparatus of claim 13, wherein the memory and computer program code are further configured to, with the processor, cause the apparatus to:

receive input defining the first operational mode that is initiated by the one or more triggers; and receive input defining the plurality of workflows for processing medication requests.

15. The apparatus of claim 14, wherein the memory and computer program code are further configured to, with the processor, cause the apparatus to:

receive the plurality of medication requests; and associate the first operational mode with a second workflow of the plurality of workflows; and process the plurality of medication requests in accordance with the first and second workflows.

16. The apparatus of claim 15, wherein the memory and computer program code are further configured to, with the processor, cause the apparatus to:

receive input defining a second operational mode that is initiated by one or more triggers;

associate the second operational mode with a third workflow of the plurality of workflows;

determine whether one of the one or more triggers of the second operational mode has occurred;

after determining that one of the one or more triggers of the second operational mode has occurred, initiate the second operational mode; and process the plurality of medication requests in accordance with the third workflow.

17. The apparatus of claim 16, wherein the memory and computer program code are further configured to, with the processor, cause the apparatus to:

associate a fourth workflow of the plurality of workflows for processing medication requests with the second operational mode; and process the plurality of medication requests in accordance with the third and fourth workflows.

18. The apparatus of claim 13, wherein each of the plurality of workflows for processing medication requests comprises (a) a patient workflow or (b) an inventory workflow.

* * * * *